US008307942B2

(12) United States Patent
Benner (10) Patent No.: US 8,307,942 B2
(45) Date of Patent: Nov. 13, 2012

(54) FLAT EARPLUG AND PACKAGE

(75) Inventor: Devin Benner, Pleasant Ridge, MI (US)

(73) Assignee: McKeon Products, Inc., Warren, MI (US)

( * ) Notice: Subject to any disclaimer, the term of this patent is extended or adjusted under 35 U.S.C. 154(b) by 0 days.

(21) Appl. No.: 12/992,691

(22) PCT Filed: May 18, 2009

(86) PCT No.: PCT/US2009/044363
§ 371 (c)(1),
(2), (4) Date: Jan. 7, 2011

(87) PCT Pub. No.: WO2009/140681
PCT Pub. Date: Nov. 19, 2009

(65) Prior Publication Data
US 2011/0094822 A1    Apr. 28, 2011

Related U.S. Application Data

(60) Provisional application No. 61/053,767, filed on May 16, 2008.

(51) Int. Cl.
*A61B 7/02* (2006.01)

(52) U.S. Cl. .......................... 181/135; 181/130; 181/131

(58) Field of Classification Search .................. 181/130, 181/131, 135
See application file for complete search history.

(56) References Cited

U.S. PATENT DOCUMENTS

| | | | | | |
|---|---|---|---|---|---|
| 2,908,343 | A | * | 10/1959 | Hummert | 181/130 |
| 3,771,521 | A | * | 11/1973 | Kittredge | 128/864 |
| 4,217,900 | A | * | 8/1980 | Wiegner et al. | 604/376 |
| 5,666,668 | A | * | 9/1997 | Ronquillo | 2/172 |
| 6,183,436 | B1 | * | 2/2001 | Korteweg et al. | 604/96.01 |
| D468,419 | S | * | 1/2003 | Vesterlund | D24/106 |
| 7,022,890 | B2 | * | 4/2006 | Sessions | 602/46 |
| 7,864,973 | B2 | * | 1/2011 | Oliveira et al. | 381/328 |
| 8,020,563 | B2 | | 9/2011 | Pfanstiehl | |
| 2007/0074991 | A1 | * | 4/2007 | Heisserer | 206/438 |
| 2009/0151735 | A1 | * | 6/2009 | Pfanstiehl | 128/864 |
| 2009/0229619 | A1 | * | 9/2009 | Chaisson et al. | 128/857 |

* cited by examiner

*Primary Examiner* — Forrest M Phillips
(74) *Attorney, Agent, or Firm* — Butzel Long (57) ABSTRACT

A flat earplug and flat earplug package assembly is provided and a method of forming a flat earplug. The flat earplug includes a flat, rectangular foam sheet having a first surface and second surface, and adapted to be rolled up upon itself to form a coiled earplug for insertion into a user's ear. An inner coil is compressed to form a rigid coil when rolled up upon itself and an outer coil expands after the coiled earplug is inserted into the user's ear. The flat earplug package assembly includes a tray container for retaining the foam sheet therein and a wrapping for enclosing the flat earplug and tray container therein.

14 Claims, 10 Drawing Sheets

FLAT EARPLUG AND PACKAGE

CROSS-REFERENCE TO RELATED PATENT APPLICATIONS

This application claims the benefit of and priority to U.S. Provisional Patent Application No. 61/053,767, filed May 16, 2008, which is incorporated by reference herein in its entirety.

BACKGROUND

The present invention relates generally to an earplug. More specifically, the present disclosure relates to a flat earplug and a package therefore.

Earplugs are often worn in environments where it is desirable to have a reduction in the ambient or environmental noise levels. For example, it may be desirable to wear earplugs in a work environment where high noise levels are generated or in other situations such as concerts wherein high noise levels may also be encountered which could cause hearing damage. However, if the person does not have earplugs with them when they need them, they are of no use.

Also, earplugs typically have a substantially cylindrical or conical shape in order to fit comfortably within the ear canal of a user. However, the cylindrical or conical earplug may easily be compressed and take a set if not stored properly, which reduces the portability and flexibility of this style of earplug. Accordingly, there is a need in the art for a flat earplug package assembly that is more convenient to carry or have on one's person at all times, such as carried in a wallet or purse, is reusable, and the earplug is adjustable according to the anatomy of the user.

SUMMARY

Accordingly, the present disclosure relates to a flat earplug, a flat earplug package assembly, and a method of forming a flat earplug.

A flat earplug includes a flat, rectangular foam sheet having a first surface and second surface, and adapted to be rolled up upon itself to form a coiled earplug for insertion into a user's ear. The coiled earplug has at least one inner coil that is compressed when rolled up upon itself and an outer coil that expands after insertion into the user's ear to retain the earplug.

A flat earplug package assembly includes a flat, rectangular foam sheet adapted to be rolled up upon itself to form a coiled earplug for insertion into a user's ear. At least one inner coil is compressed when the foam sheet is rolled up upon itself to form the coiled earplug and an outer coil that expands after the earplug is inserted into the user's ear. The flat earplug package assembly further includes a tray container for retaining the foam sheet therein and a wrapping for enclosing the flat earplug and tray container therein.

The method of forming a flat earplug includes the steps of providing a foam sheet having a first surface and a second surface, and a predetermined thickness; removing a backing from a foam sheet having a first end and a second end; rolling the foam sheet upon itself from the first end of the foam sheet to the second end of the foam sheet to form a substantially cylindrically shaped coiled earplug; adjusting a diameter of each coil of the earplug by compressing the foam sheet as it is rolled upon itself; and placing the coiled earplug into an ear canal of a user's ear, such that the coiled earplug expands and is retained within the user's ear. The method further includes the steps of removing the coiled earplug from the user's ear and unrolling the coiled earplug back into the flat earplug; and placing the flat earplug back into the tray container for later reuse.

One advantage of the present disclosure is that the flat earplug package assembly is provided that is portable, more compact and allows for easier storing, such as in a wallet. Another advantage of the present disclosure is that the size of the flat earplug is customizable to the user by adjusting the number of coils. Still another advantage of the present disclosure is that the flat earplug quickly returns to its nominal thickness after removal from the package. A further advantage of the present disclosure is that the flat earplug is reusable and is protected within the package assembly. Still a further advantage of the present disclosure is that the flat earplug package distributes forces on the earplug in a uniform manner while in contained in the package. Yet a further advantage of the present disclosure is that the flat earplug can be die cut from a piece of foam material. Still yet a further advantage of the present disclosure is that the flat earplug is cost effective to manufacture and reduces material scrappages.

Other features and advantages of the present disclosure will be readily appreciated, as the same becomes better understood after reading the subsequent description taken in conjunction with the accompanying drawings.

DETAILED DESCRIPTION

Figure 1:
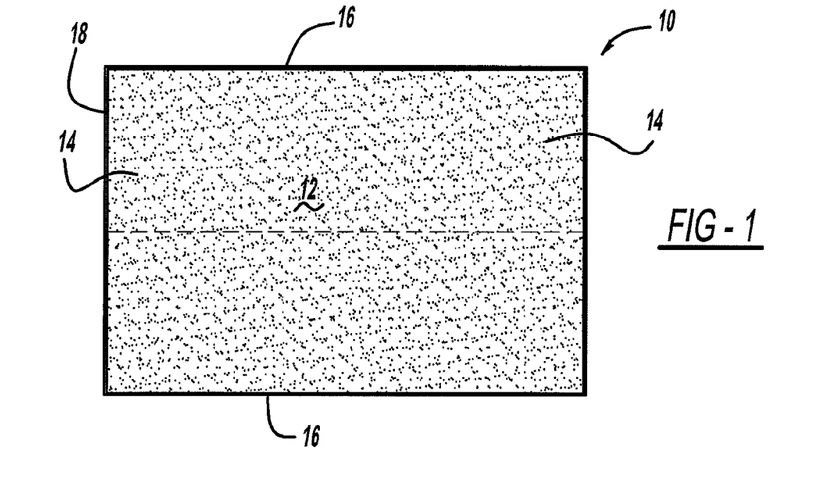
FIG. 1 is an elevational top view of a flat earplug package, according to an exemplary embodiment.
Figure 2:
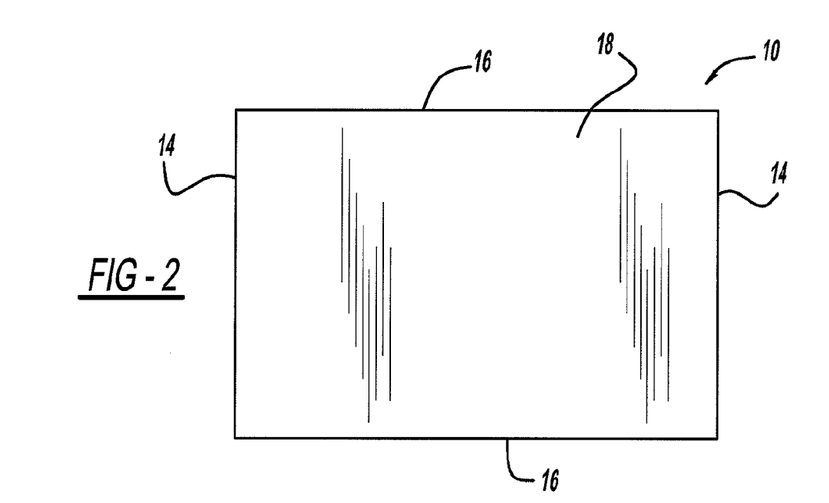
FIG. 2 is a plan bottom view of the flat earplug package of FIG. 1, according to an exemplary embodiment.

Referring to FIGS. 1-11, a flat earplug assembly is generally shown at 10. The flat earplug 12 has a substantially rectangular shape and is defined by ends 14 and sides 16. The flat earplug 12 is generally flat in cross section. The flat earplug 12 may be mounted or affixed to an optional backing or release sheet 18, as shown in FIG. 2 to form the flat earplug assembly 10. The flat earplug 12 may be inserted into an ear canal of a user's ear.

Figure 3:
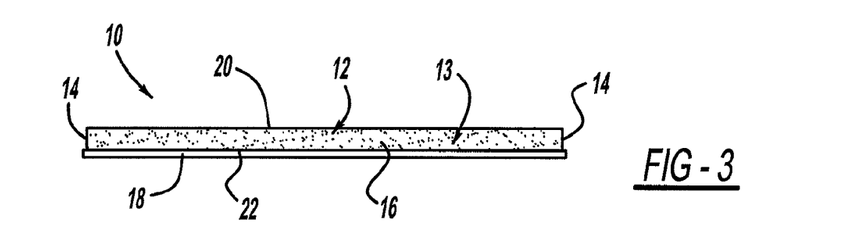
FIG. 3 is an elevational side view of the flat earplug package of FIG. 1, according to an exemplary embodiment.

The flat earplug 12 is formed from a sheet of foam material 13, such as an open cell foam material. Referring to FIG. 3, the foam sheet 13 has a first surface 20 and a second surface 22, and an open cell foam layer 24 disposed therebetween. An example of a foam material includes urethane, polyvinylchloride, etc. Another example of a material used to make the foam sheet is a Food and Drug Administration (FDA) approved foam. The foam sheet 13 is manufactured utilizing methods and techniques typically known by those of ordinary skill in the art. The flat earplugs 12 may be fabricated from a foam sheet 13 having a perforation or cut that divides the foam sheet 13, such as into two halves. When the foam sheet is 13 separated or pulled apart along the perforation or cut, two halves are created which now provide two separate flat earplugs 12 that may be used for both the left and right ear of the user, as shown in FIGS. 5 through 8.

Figure 4:
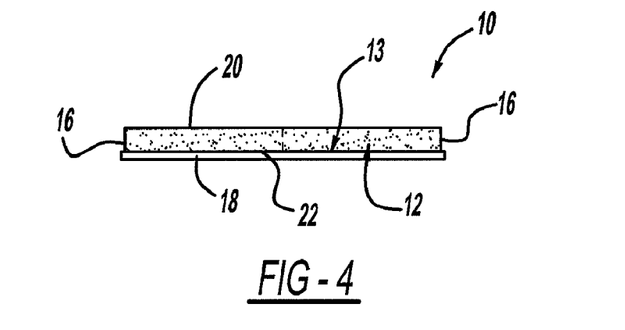
FIG. 4 is an elevational end view of the flat earplug package of FIG. 1, according to an exemplary embodiment.
Figure 5:
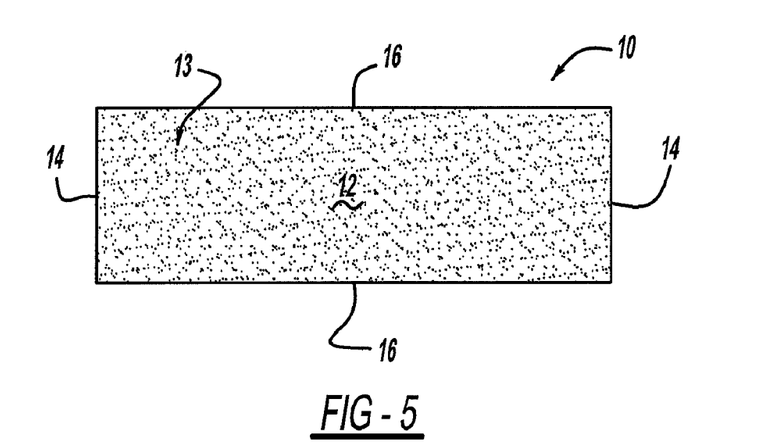
FIG. 5 is an elevational top view of a flat earplug, according to an exemplary embodiment.
Figure 6:
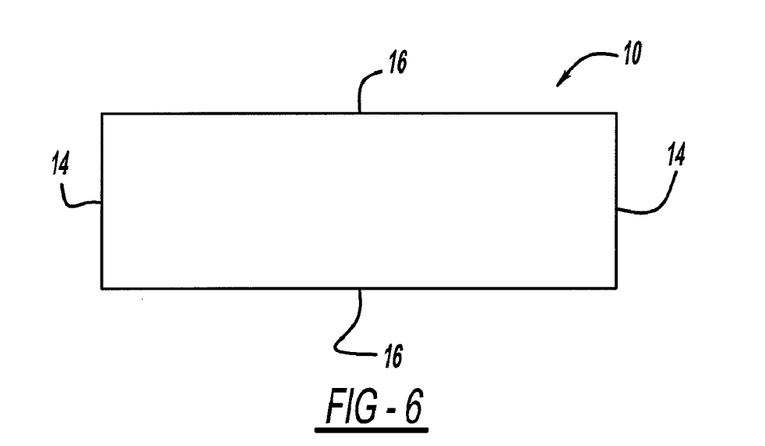
FIG. 6 is an elevational bottom view of the flat earplug of FIG. 5, according to an exemplary embodiment.
Figure 7:
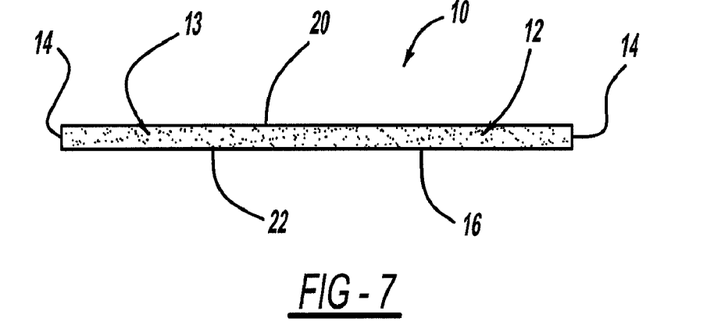
FIG. 7 is an elevational side view of the flat earplug of FIG. 5, according to an exemplary embodiment.
Figure 8:
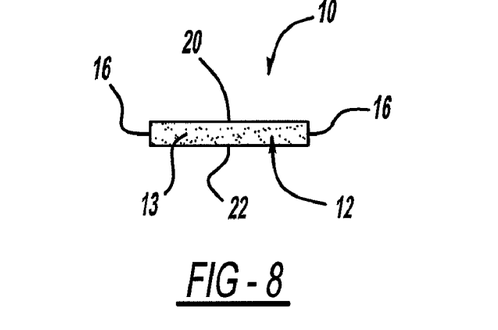
FIG. 8 is an elevational end view of the flat earplug of FIG. 5, according to an exemplary embodiment.

The foam sheet 13 can be manufactured in such a way so as to provide both of the surfaces 20 and 22 of the flat earplug 12 with a generally cellular texture as shown in FIG. 1. Alternatively, the foam sheet 13 can be constructed so as to provide either surface 20 or surface 22 with a substantially smooth skin or finished surface, as shown in FIG. 3. The smooth or finished surface has a more closed cellular structure than that of the inner layer. FIG. 4 illustrates a flat ear plug 12 formed from a foam sheet 13 whereby both surfaces 20, 22 include a substantially smooth surface or skin disposed thereon. For example, the foam sheet 13 may be die cut from a larger piece of foam material, and the foam material may have a first or second surface that is "skinned".

In an example of a foam sheet 13 whereby at least one surface 20, 22 includes a skin thereon, the skin preferably provides a semi-adhesive, adhesive, or tacky property to the surface. Therefore, when the flat earplug 12 is rolled upon itself to form the coiled earplug, the skin associated with either surface 20, surface 22, or both surfaces, allows the surfaces 20, 22 to partially adhere to one another as coils are being formed and/or resist sliding or movement therebetween. The semi-adhesive property can be intrinsic to the skin formed on the surface 20, surface 22, or both surfaces, or can be an adhesive coating applied to either surface 20, surface 22, or both. The adhesive may be a weak, non-permanent adhesive, such as an FDA approved adhesive.

Figure 9:
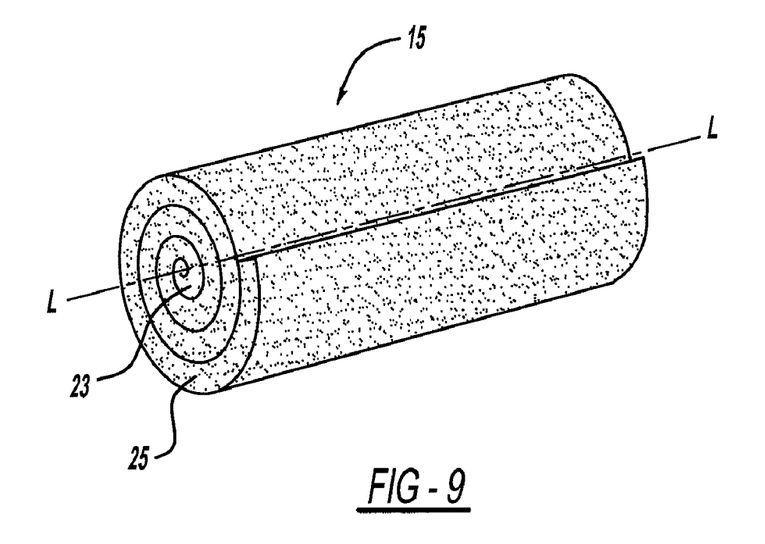
FIG. 9 is a front elevational view of a rolled flat earplug, according to an exemplary embodiment.

The skin disposed on either surface 20, surface 22, or both, provides the earplug 10 with a longitudinally extending rigidity along the line L-L as shown in FIG. 9. That is, when the flat earplug 10 is rolled into a coil, the first coil 23 is compressed to form an inner core that may be rigid that facilitates in insertion of the coiled earplug 15. Each successive coil may be under less compression than the first coil 23, and may also facilitate insertion and expand after insertion. The last or outer coil 25 may be compressible before insertion and expandable after insertion to custom fit the coiled earplug 15 according to the particular anatomy of the user. The skin disposed on either surface 20, surface 22 or both, further imparts the earplug 10 with the ability to resist compression and/or deformation in the direction along the line defined by L-L. This rigidity and/or resistance to compression along the line L-L, allows the earplug 10 to be more easily inserted into the ear of the user, without flattening out during insertion.

The substantially semi-adhesive properties of the foam sheet 13 and/or of the skin on either surface 20 and/or surface 22 also provides the user of the earplug 10 with the ability to adjust both the size and/or comfort of the earplug 10. Because of the semi-adhesive property of the foam used to make the foam sheet 13 and/or the adhesive properties of the surfaces 20, 22, the user of the earplug 10 can adjust the overall size or diameter of the earplug by varying the tightness by which they spirally roll the foam sheet 13 from the first end 14 to the opposite end 14, and the number and size of coils, with the inner coil 23 being the most compressed and the outer coil 25 the least compressed. In addition, the adhesive characteristic of the surface layer enhances the rigidity of the flat earplug 12, and assists in retaining a coiled shape of the flat earplug 12 when inserted into a user's ear in a manner to be described. Further, the adhesive characteristic enhances reusability of the flat earplug 12, or readjustment of the flat earplug 12 or the like in use to accommodate the individual user's ear canal shape and size.

The flat earplug 12 may be secured to a backing or release sheet 18. The backing or release sheet 18 can be any suitable material, such as paper, coated paper, cardboard, plastic foil, or the like. In addition, the backing or release sheet 18 may incorporate information, such as instructions, warnings, advertising, logos, images, or other indicia, or the like, printed thereon.

Figure 12:
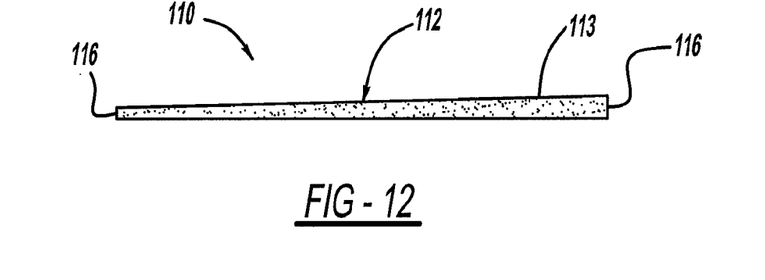
FIG. 12 is a side view of another embodiment of the flat earplug, the opposed side being a mirror image thereof.
Figure 13:
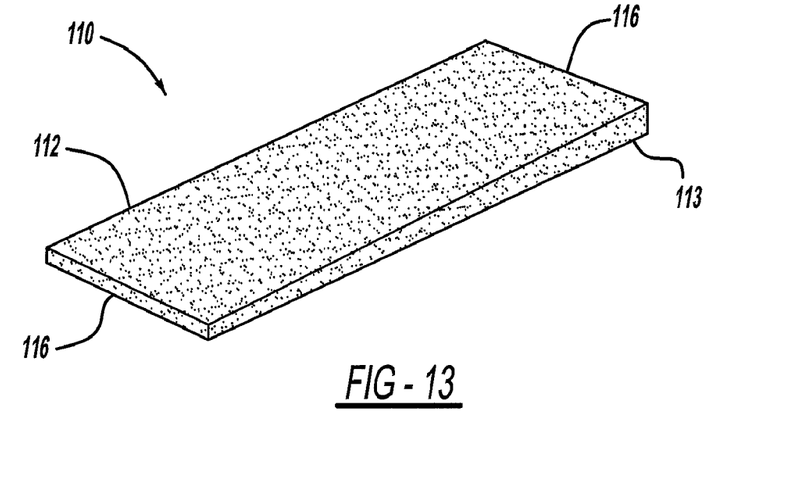
FIG. 13 is an elevational end view thereof, the opposed end being a minor image.
Figure 14:
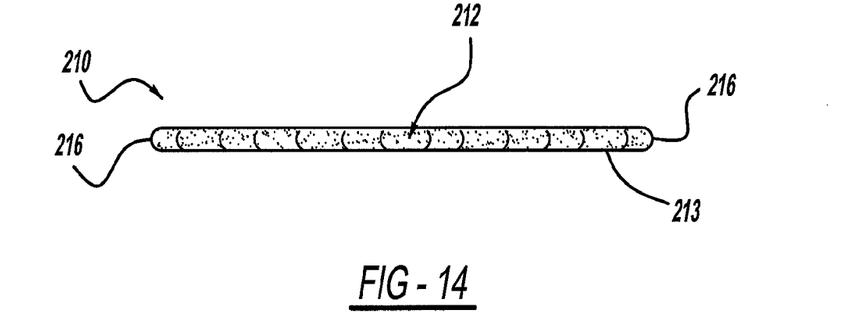
FIG. 14 is an elevational side view of another embodiment of the flat earplug, the opposed side being a minor image thereof.
Figure 15:
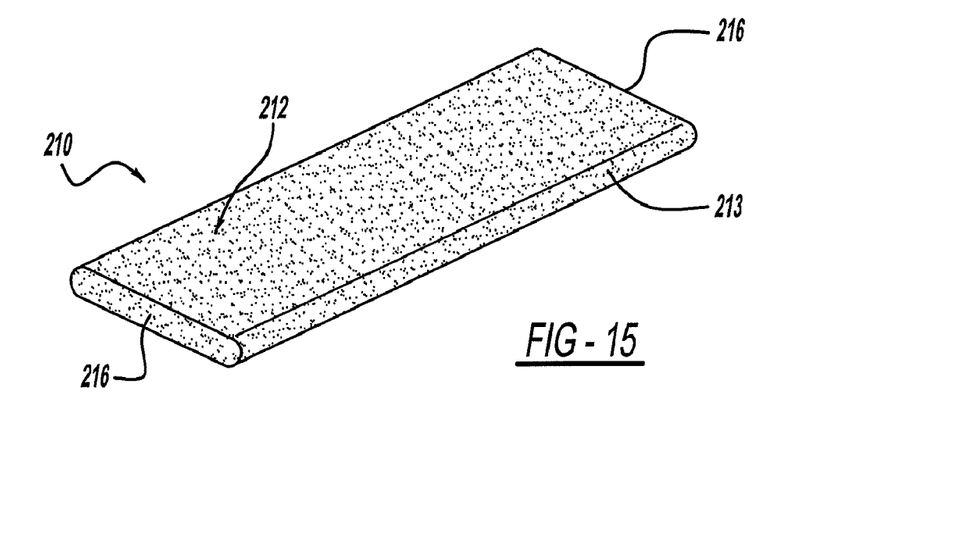
FIG. 15 is an elevational end view thereof, the opposed end being a minor image.
Figure 16:
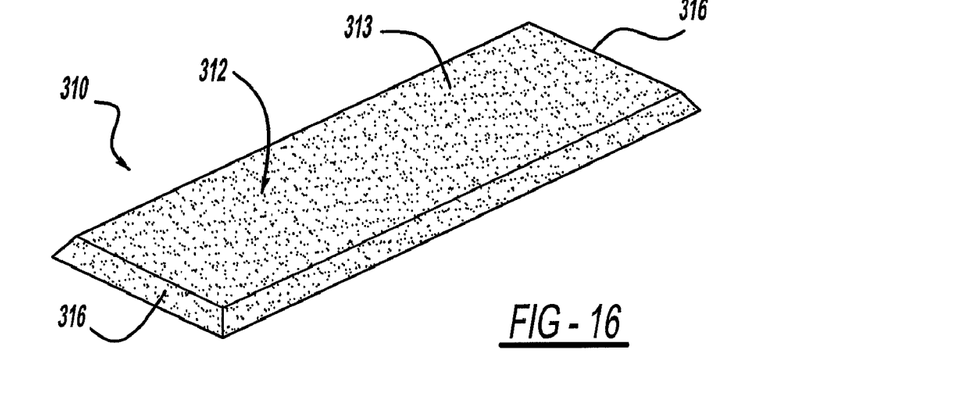
FIG. 16 is a perspective view of a further embodiment of the flat ear plug.
Figure 17:
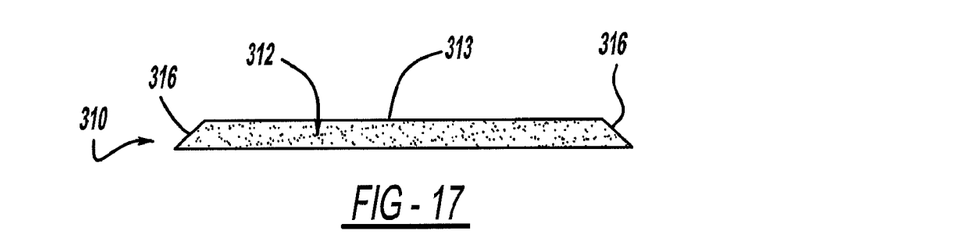
FIG. 17 is an elevational side view thereof, the opposed side being a minor image.
Figures 18, 19:
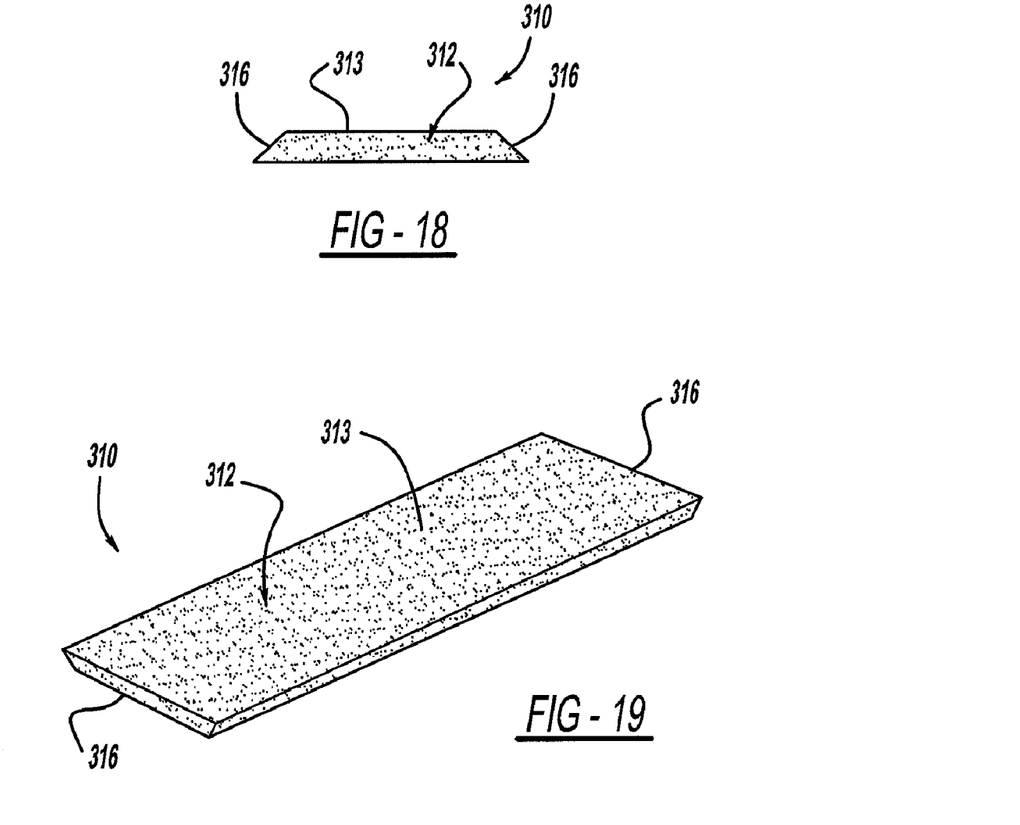
FIG. 18 is an elevational end view thereof, the opposed end being a minor image.
FIG. 19 is a perspective view of still a further embodiment of the flat earplug.
Figure 20:
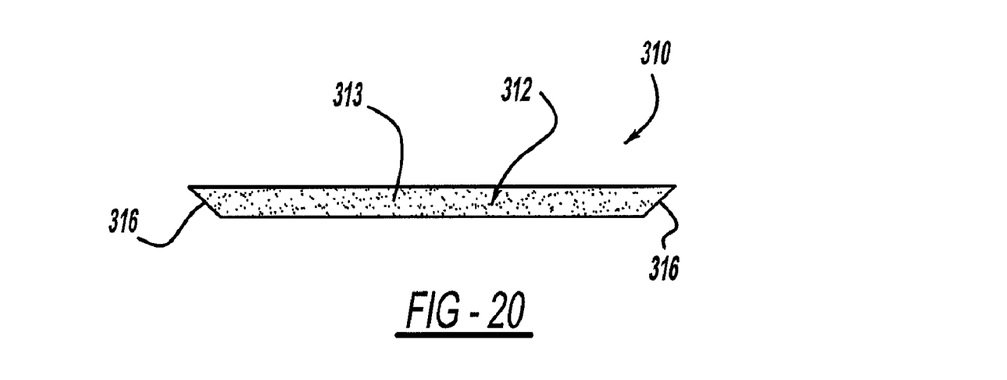
FIG. 20 is a is an elevational side view thereof, the opposed side being a mirror image.
Figure 21:
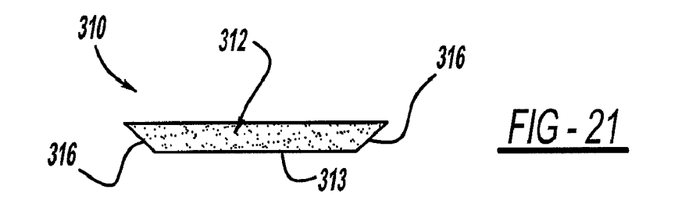
FIG. 21 is an elevational end view thereof, the opposed end being a mirror image.

Other examples of a flat earplug 12 are shown in FIGS. 12 through 21. Like reference number have like numbers increased by 100. The sides 16 of the foam sheet 13 can have various profiles to accommodate additional comfort and/or fit. Referring to FIGS. 12 and 13, the foam sheet 112, alternatively can include a slight taper from one side 116 to the other side 116 in order to facilitate the generation of a predetermined shape, such as a "cone-shaped" earplug 110 upon rolling of the foam sheet 113. The taper may be gradual, tapered profile from one side 116 to the other side 116 wherein both sides 116 have a straight profile and the length of one side 116 is shorter than the other side 116. As shown in FIGS. 14 and 15, the foam sheet 213 may have at least one side 216 that includes a rounded profile. Referring to FIG. 16 through 21, the foam sheet 313 may have at least one side 316 that includes a beveled profile. Alternatively, both sides 316 may include a beveled profile. As shown in FIGS. 1 through 8, both sides 16 can have a straight profile.

Figure 22:
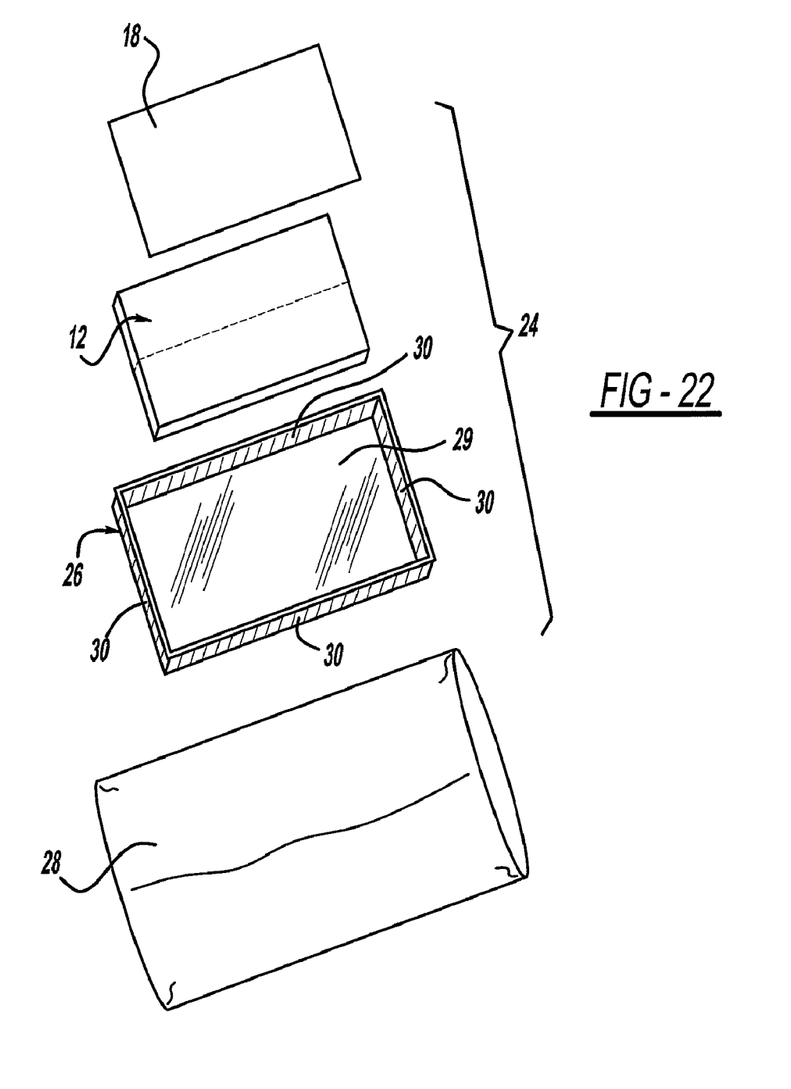
FIG. 22 is an exploded perspective view of a flat earplug package assembly, according to an exemplary embodiment.

Referring to FIG. 22, a flat earplug package assembly 24 is illustrated. The flat earplug package assembly 24 may include the flat earplug 12, the backing or release sheet 18, the earplug tray container 26, or an outer cover or wrapping. The flat earplug 12 is placed into the earplug tray container 26 which then may be placed within a protective wrapping 28 to complete the package assembly 24.

Figure 23:
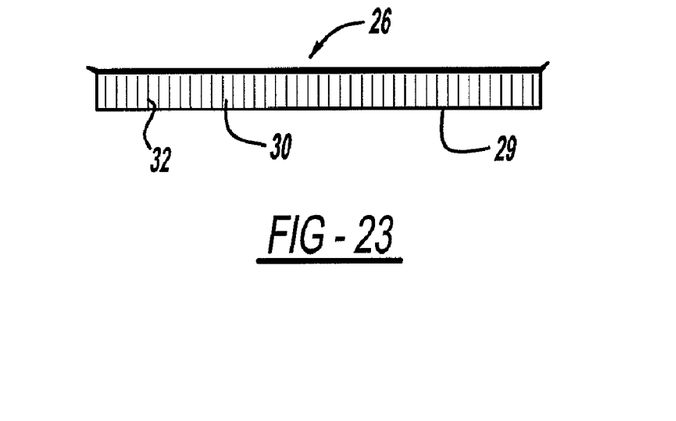
FIG. 23 is a side view of the flat earplug tray container, according to an exemplary embodiment.
Figure 24:
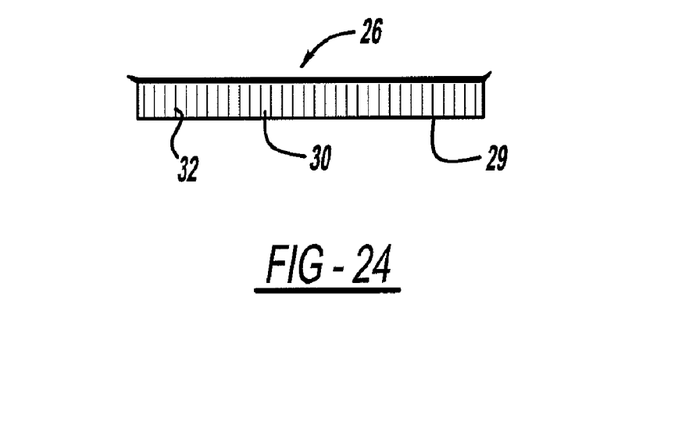
FIG. 24 is a front view of the flat earplug tray container, according to an exemplary embodiment.

Referring to FIGS. 23 through 24, the earplug tray container 26 is illustrated. The tray container 26 includes a base wall 29 and side walls 30 extending upwardly from an edge of the base wall 29. The base wall 29 may be a solid wall, or it may have a centrally located opening. The tray container 26 may be fabricated from a material (e.g., plastic, paper, cut piece of extruded plastic, recycled or the like) and is constructed to generally have the same size and shape of a pair of flat earplugs 12. In an example, the flat earplug 12 may be placed snugly within the earplug tray container 26.

Figure 25:
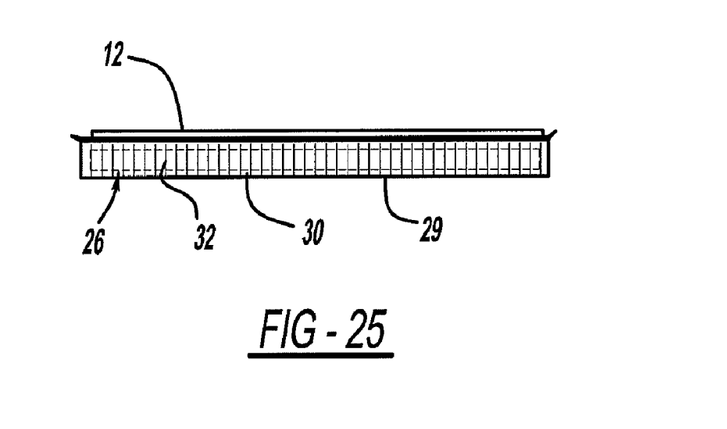
FIG. 25 is a side view of the flat ear plug tray container including a flat earplug placed therein, according to an exemplary embodiment.

The side walls 30 of the earplug tray container 26 may have a predetermined height. For example, the predetermined height may be slightly less than the height of sides 14, 16 of the flat earplug 12, so that a predetermined depth of the flat earplug 12 is above the walls 30, as shown in FIG. 25 at 27. For example, the height of the walls 30 may be up to 25% less than the corresponding depth of the flat earplug 12 and card (if utilized). The flat earplug 12 may be slightly compressed when placed within a wallet for example, but the walls 30 ensure that the flat earplug 12 is not compressed over a predetermined amount so that the flat earplug 12 quickly returns to it's original dimensions after removal from the tray 26. For example, if the foam material is compressed by more than 25%, the material may acquire a significant set over time. In another example, if the compression of the material is less than 25%, the set may be less than 4%. If the material acquires too great of set, the elasticity of the material and its ability to recover over time is influenced. (i.e., flat earplug's ability to compress and decompress during use). The flat earplug 12 may be compressed slightly due to the lower height of the walls 30, however, this slight compression may compensate for any dimensional tolerances inherent in the foam material. The walls 30 of the earplug tray container 26 may also have a plurality of ribs 32 which provide additional rigidity to the walls 30 of the earplug tray container 26 and thereby further prevent excessive compression of the flat earplug 12. Some compression of the flat earplug 12 can occur when the flat ear plug assembly 24 is stored within another object, such as when placed in a wallet or the like. However, the resiliency of the foam returns the flat ear plug 12 back to it's original size and shape.

The protective wrapping 28 may be manufactured from any suitable material (e.g., plastic, paper, etc.) and has dimensions that are preferably slightly larger than the foam sheet 12, optional backing or release sheet 18, and the earplug tray container 26 so that these items may be placed snugly therein and thereby form a relatively small and compact package assembly 24. The protective wrapping 28 protects the flat earplug 10 from damage, from the elements (e.g., moisture, etc.) and keeps the flat earplug 12 clean, sterile and free of debris (e.g., dust, etc.).

Figure 26:
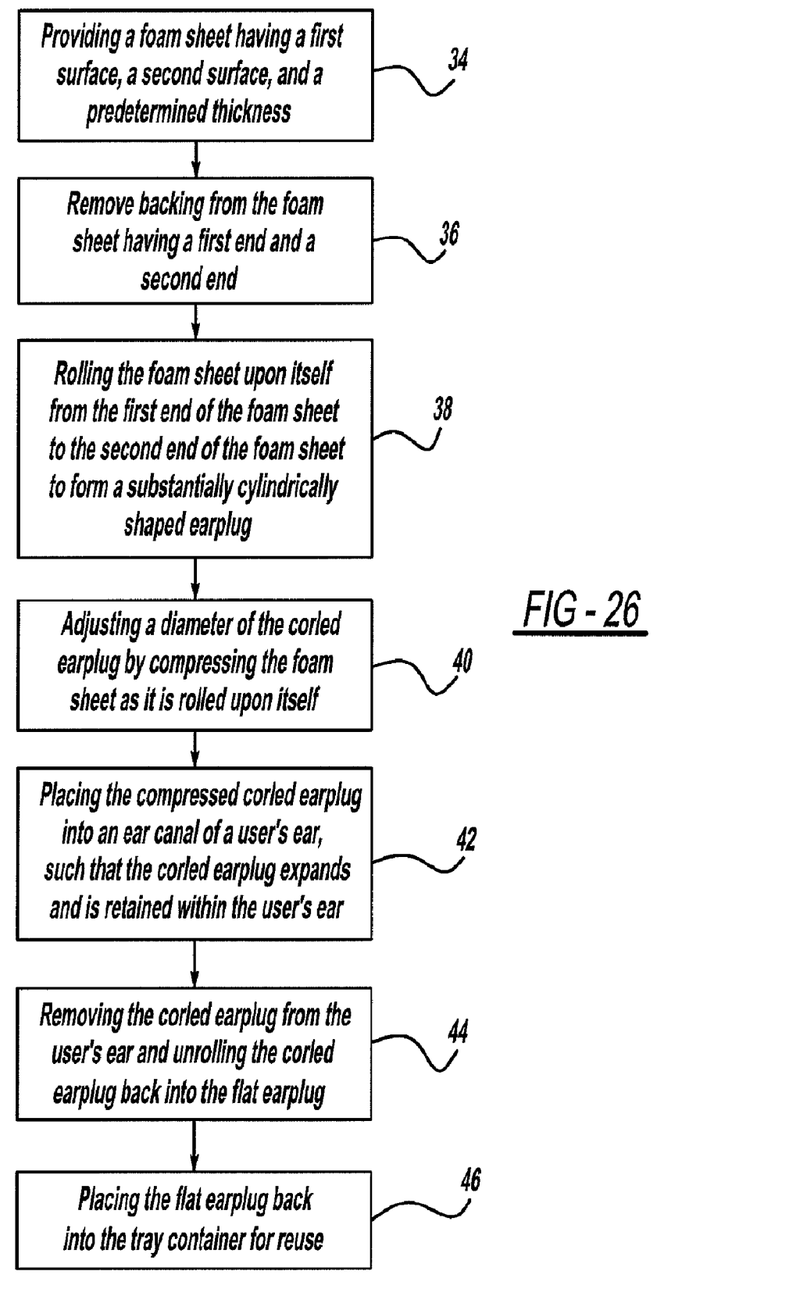
FIG. 26 is a flow chart of the method of using the flat earplug, according to an exemplary embodiment.

Referring now to FIG. 26, a flow chart of the method of using the flat earplug assembly 12 is shown. The first step 34, includes providing a foam earplug assembly 10 having a pair of foam earplugs 12 positioned on a sheet 18 and placed within a tray 26. For example, by placing the flat earplug 12 with the card opposite the tray base wall 29, the flat earplug 12 is further protected since any forces on the ear plug package 24 are distributed more evenly. In a second step 36 the flat earplug 12 is removed from the tray 26 and from the backing or release sheet 18.

Figure 10:
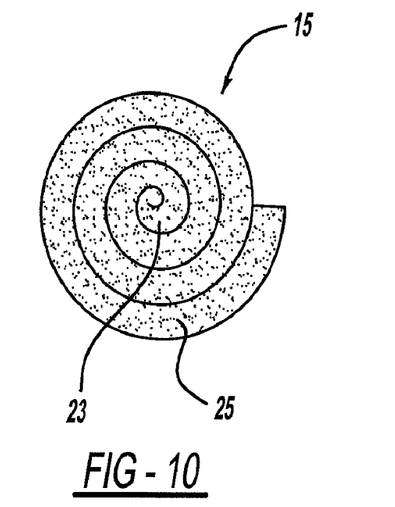
FIG. 10 is an elevational end view of the rolled flat earplug of FIG. 9, according to an exemplary embodiment.
Figure 11:
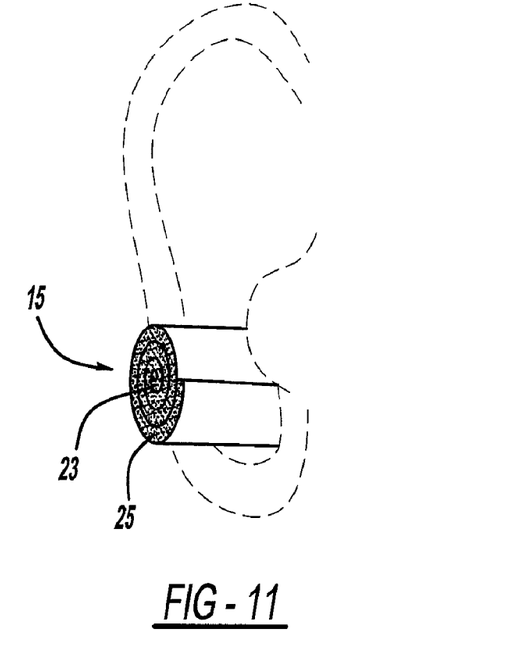
FIG. 11 is a perspective front view of the rolled flat earplug of FIG. 9 partially inserted within an ear canal of a user's ear, according to an exemplary embodiment.

In a third step 38, the foam sheet 13 is rolled or coiled into a spiral from the first end 14 to the opposite end 14, as shown in FIGS. 9 and 10. The first coil 23 is compressed to form a rigid inner core that assists in retention of the earplug shape and insertion in the user's ear. The middle and outer coils may also assist in retaining the longitudinal shape of the earplug during insertion, due to the rigid frame formed by the skin to skin contact of the foam material. In the fourth step 40, the diameter of the coiled earplug 15 may be adjusted depending on the size and shape of the user's ear canal, by the amount of compression used in forming each coil as the foam sheet 13 is rolled upon itself into a spiral. Upon rolling of the foam sheet 13 from the first end 14 to the opposite end 14, foam sheet 13 becomes a substantially cylindrically shaped coiled earplug 15, as shown in FIG. 9. The outer coil 25 is compressible before, and expandable after insertion. The coils may also be further compressed during insertion. At least one end 14 can be tapered in order to provide a smooth transition when the foam sheet 13 is rolled in a spiral manner onto itself to impart additional comfort to the user of the earplug 12. In addition, the finished surface 20, 22 can enhance comfort of the earplug in the user's ear.

In a fifth step 42, the compressed coiled earplug 15 is placed into an ear canal of a user's ear, such that the coiled earplug 15 compresses and expands according to the size and shape of the user's ear in order to be retained within the user's ear. For example, the user grasps the upper end of the ear, and gently pulls the ear in an upwardly direction. The coiled earplug 15 is placed in the ear such that the coils are oriented in a coiled direction, such as a clockwise direction. The user turns or spins the coiled earplug 15 in the coiled or clockwise direction of this example while inserting the earplug 15, in order to locate the earplug within the ear canal. The outer coil 25 may compress and then expand to fit the ear canal. Some of the middle coils may also compress and then expand, depending on how tightly they were compressed and the anatomy of the user's ear. In a sixth step 44, the coiled earplug 15 is removed from the user's ear and unrolled. In a seventh step 46, the now flat earplug 12 may be placed back on the card 18 and/or placed back into the tray container 26 for later reuse.

The present disclosure has been described in an illustrative manner. It is to be understood that the terminology which has been used is intended to be in the nature of words of description rather than of limitation.

What is claimed is:

1. A flat earplug comprising:
    A flat, rectangular foam sheet of one layer of open cell foam material having a first surface and a second surface and a first end that is rolled up upon itself to form a coiled earplug of contiguous coils for blocking sound form entering a user's ear;
    Wherein the coiled earplug includes an inner most coil that is compressed to form a rigid axial core when the first end of the foam sheet is rolled upon itself to form the coiled earplug; and
    Successively contiguous outer coils that immediately surround the innermost coil, the outer coils being compressible before and expandable after the coiled earplug is inserted into the user's ear, to retain the earplug in the user's ear, wherein either the first or second surface has a skin thereon, and wherein the skin has at least one of a smooth, a semi-adhesive, or an adhesive texture.

2. The flat earplug of claim 1, wherein the foam sheet includes a first, second, third and fourth side, the sides having a profile.

3. The flat earplug of claim 2, wherein the profile is at least one of straight, rounded, or beveled.

4. The flat earplug of claim 1, wherein the foam sheet includes a first and second end.

5. The flat earplug of claim 4, wherein the foam sheet is tapered from the first end to the second end.

6. The flat earplug of claim 1, further comprising a backing positioned adjacent a second surface of the foam sheet.

7. The flat earplug of claim 6, wherein the backing includes indicia printed thereon.

8. A flat earplug package assembly comprising:

A flat, rectangular foam sheet of one layer of open cell foam material having a first end that is rolled up around the first end to form a coiled earplug of contiguous coils for blocking sound from entering a user's ear, wherein either the first or second surface has a skin thereon, and wherein the skin has at least one of a smooth, a semi-adhesive, or an adhesive texture , and the coiled earplug includes an innermost coil that is compressed to for a rigid axial core when the foam sheet is rolled upon itself and a contiguous outer coil that is compressible before and expandable after the coiled earplug is inserted into the user's ear to retain the earplug in the user's ear; and A tray container for retaining the foam sheet therein.

9. The flat earplug package assembly of claim 8, wherein the tray container includes a wall having a predetermined height that is less than a height of the foam sheet.

10. The flat earplug package assembly of claim 9, wherein the wall includes a plurality of ribs for added rigidity.

11. The flat earplug package assembly of claim 8, further comprising a wrapping that encloses the foam sheet and tray container.

12. A method of forming a flat earplug that comprises the steps of:

Providing a foam sheet having a first surface and a second surface; and a first end and a second end, and a predetermined thickness, wherein either the first or second surface has a skin thereon, and wherein the skin has at least one of a smooth, a semi-adhesive, or an adhesive texture; removing a backing from the foam; rolling the foam sheet upon itself from the first end of the foam sheet to the second end of the foam sheet to form a substantially cylindrically shaped coiled earplug having an innermost coil that is compressed to form a rigid axial core and successively contiguous outer coils that surround the innermost coil and are compressible and expandable;

adjusting a diameter of the coiled earplug by compressing the foam sheet while forming the successively contiguous outer coils around the rigid axial core as it is rolled upon itself; and placing the compressed coiled earplug into an ear canal of a user's ear, such that tile outer coils expand and the coiled earplug is retained within the user's ear to block sound from entering the user's ear.

13. The method of forming a flat earplug of claim 12, further comprising the step of:

removing the coiled earplug from the user's ear and unrolling the coiled earplug back into the foam sheet.

14. The method of forming a flat earplug of claim 12, further comprising the step of:

placing the foam sheet back into the tray container for later reuse.

* * * * *